United States Patent [19]

Shamshoum et al.

[11] Patent Number: 5,030,786
[45] Date of Patent: Jul. 9, 1991

[54] LIQUID PHASE AROMATIC CONVERSION PROCESS

[75] Inventors: Edwar S. Shamshoum, Houston; James T. Merrill, Katy, both of Tex.

[73] Assignee: Fina Technology, Inc., Dallas, Tex.

[21] Appl. No.: 371,581

[22] Filed: Jun. 23, 1989

[51] Int. Cl.$^5$ .......................... C07C 5/22; C07C 5/52
[52] U.S. Cl. .................................. 585/467; 585/475; 585/448
[58] Field of Search ....................... 585/467, 475, 448

[56] References Cited

U.S. PATENT DOCUMENTS

| | | |
|---|---|---|
| 3,551,510 | 12/1970 | Pollitzer . |
| 4,107,224 | 8/1975 | Dwyer . |
| 4,185,040 | 1/1980 | Ward et al. . |
| 4,197,214 | 4/1980 | Chen et al. . |
| 4,301,316 | 11/1981 | Young . |
| 4,324,940 | 4/1982 | Dessau ................................. 585/467 |
| 4,459,426 | 7/1984 | Inwood et al. ....................... 585/467 |
| 4,469,908 | 9/1984 | Burress ................................ 585/467 |
| 4,551,438 | 11/1985 | Miller ..................................... 502/66 |
| 4,740,648 | 4/1988 | Rabo et al. . |
| 4,774,377 | 9/1988 | Barger et al. ........................ 585/475 |

FOREIGN PATENT DOCUMENTS

| | | |
|---|---|---|
| 0007126 | 1/1980 | European Pat. Off. ............ 585/467 |
| 7407433 | 12/1974 | Netherlands ........................ 585/467 |
| 0778014 | 7/1957 | United Kingdom ................ 585/467 |
| 1273252 | 3/1972 | United Kingdom ................ 585/467 |

OTHER PUBLICATIONS

Aldrich Chemical Catalog, (1988–1989), page 1250 #20, 821-3.

Primary Examiner—Helen M. S. Sneed
Assistant Examiner—James Saba
Attorney, Agent, or Firm—Joseph A. Schaper; William D. Jackson; John K. Abokhair

[57] ABSTRACT

Aromatic conversion processes employing zeolite Y, zeolite omega and zeolite beta molecular sieve catalyst. A feed stock containing at least one aromatic compound and having water entrained therein is passed to a dehydration zone. In the dehydration zone, water is removed to provide a dehydrated feed stock of a water content no more than 100 ppm, preferably 50 ppm or less. The dehydrated feed stock is then supplied to the reaction zone containing the molecular sieve catalyst selected from the group consisting of zeolite Y, zeolite omega, and zeolite beta. The reaction zone is operated at temperature and pressure conditions to maintain the reactor contents in the liquid phase and also sufficient to cause the conversion reaction to proceed in the presence of the catalyst. Specific conversion processes include the ethylation of benzene under liquid-phase conditions to produce ethylbenzene and the transalkylation of a feed stock containing a mixture of a polyalkylbenzene component and a benzene component to produce a disproportionation product comprising a monoalkylbenzene.

16 Claims, 1 Drawing Sheet

5,030,786

LIQUID PHASE AROMATIC CONVERSION PROCESS

FIELD OF THE INVENTION

This invention relates to liquid phase aromatic conversion processes carried out over zeolite molecular sieve catalysts and more particularly to such processes carried out under liquid phase conditions in which the feed stock is dehydrated to provide a feed of reduced water content.

BACKGROUND OF THE INVENTION

The use of molecular sieves as catalysts in aromatic conversion processes are well known in the chemical processing and refining industry. Aromatic conversion reactions of considerable commercial importance include the alkylation of aromatic compounds such as in the production of ethyltoluene, xylene, ethylbenzene, cumene or higher alkyl aromatics and in disproportionation reactions such as toluene disproportionation, xylene isomerization, or the transalkylation of polyalkylbenzenes to monoalkylbenzenes.

Various aromatic conversion processes may be carried out either in the liquid phase, the vapor phase or under conditions under which both liquid and vapor phases exist. At the relatively high temperatures involved in vapor phase reactions, it is generally accepted that water present in the feed stream is detrimental to the reaction process, while various reasons are advanced for the adverse impact of water, the most widely observed detrimental effect is probably catalyst deactivation due to dealumination. For example, U.S. Pat. No. 4,197,214 to Chen et al. discloses a process for modifying various crystalline zeolite molecular sieves such as ZSM-5, ZSM-11, ZSM-12, ZSM-35, ZSM-38, faujasite, mordenite, and erionite by the inclusion of metallic ions such as zinc. Chen et al. states that high temperature steam functions by way of a hydrolysis reaction to cause loss of framework aluminum which is accompanied by the loss of the associated protons, leading to a reduction in catalytic activity. The hydrolysis reaction is said to be quite slow at temperatures below about 800° F. However, at higher temperatures above 900° F., the reaction rate is sufficiently fast to affect long-term stability of the zeolite catalyst.

In some cases, water can be tolerated under the high temperature conditions involved in vapor phase reactions. For example, U.S. Pat. No. 4,107,224 to Dwyer discloses the vapor phase ethylation of benzene over zeolite catalysts characterized in terms of those having a constraint index within the approximate range of 1-12. Suitable zeolites disclosed in Dwyer include ZSM-5, ZSM-11, ZSM-12, ZSM-35 and ZSM-38. The Dwyer process involves the interstate injection of ethylene and benzene to offset some of the temperature rise due to the exothermic alkylation reaction. Dwyer states that water and hydrogen sulfide are tolerable if more rapid aging of the catalyst is acceptable, but are moderately detrimental in the process.

Steam stabilized zeolites are disclosed as useful in aromatic conversion processes involving alkylation such as in the production of ethylbenzene or cumene. For example, U.S. Pat. No. 4,185,040 to Ward et al. discloses the alkylation of benzene to produce ethylbenzene or cumene employing zeolites such as molecular sieves of the X, Y, L, B, ZSM-5 and Omega crystal types, with steam stabilized hydrogen Y zeolite being disclosed as the preferred catalyst. In the Ward process, temperature and pressure conditions are employed so that at least some liquid phase is present until substantially all of the alkylating agent is consumed. Ward states that rapid catalyst deactivation occurs under most operating conditions when no liquid phase is present.

The use of steam stabilized zeolites in the production of high molecular weight alkyl benzenes is disclosed in U.S. Pat. No. 4,301,316 to Young. Here relatively high molecular weight alkylating agents having one or more reactive alkyl groups of at least 5 carbon atoms are employed. The reactants may be in either the vapor phase or the liquid phase. The zeolite catalyst may be subjected to modifying treatments involving steaming for periods ranging from about one quarter to about 100 hours in an atmosphere containing from about 5 to about 100% steam.

U.S. Pat. No. 4,774,377 to Barger et al. discloses an aromatic conversion process involving alkylation over a catalyst comprising a solid phosphoric acid component followed by transalkylation aluminosilicate molecular sieve transalkylation catalysts including X-type, Y-type ulstrastable Y, L type, Omega type and mordenite zeolites. Aluminosilicate alkylation catalysts may also be employed. Water in an amount from about 0.01 to 6% by volume of the organic material charged to the alkylation reaction zone may be added. The water is typically removed with the light by-product stream recovered in the first separation zone.

In hydrocarbon conversion processes involving olefin conversion, water may or may not be tolerated in the feed stream depending on the nature of the molecular sieve employed. For example, U.S. Pat. No. 4,551,438 to Miller discloses the oligomerization of olefins over molecular sieves, characterized as intermediate pore size, having an effective pore aperture in the range of about 5 to 6.5 angstroms, such as ZSM-5, ZSM-11 and silicalite, Miller discloses that the feed should be contain less than 100 ppm and preferably less than 10 ppm water as well as being low in sulfur and nitrogen. On the other hand, when employing a somewhat larger pore size molecular sieve, specifically steam stabilized zeolite Y, in the conversion of $C_2$–$C_{12}$ olefins to motor fuels, water is described as an effective cofeed which stabilizes the catalyst and reduces the deactivation rate. Thus, as described in U.S. Pat. No. 4,740,648 to Rabo et al., co-fed water is described as a particularly desirable diluent which tends to aid in resistance of zeolite Y catalyst to coking and aging.

SUMMARY OF THE INVENTION

In accordance with the present invention, there is provided a process useful in carrying out liquid phase aromatic conversion employing a zeolite molecular sieve catalyst having a pore size greater than 6.5 angstroms. In carrying out the invention, a feed stock containing at least one aromatic compound and having water entrained therein is passed to a dehydration zone. In the dehydration zone, water is removed to provide a dehydrated feed stock of a water content no more than 100 ppm, preferably 50 ppm or less. The dehydrated feed stock is then supplied to the reaction zone containing the molecular sieve catalyst which is selected from the group consisting of zeolite Y, and zeolite beta. The reaction zone is operated at temperature and pressure conditions to maintain the reactor contents in the liquid phase and also sufficient to cause the conversion reaction to proceed in the presence of the catalyst.

One embodiment of the invention involves the liquid phase alkylation of an aromatic substrate with the dehydration of the feed stock to reduce the water content to no more than 100 ppm as described above. A specific application of the invention is in the ethylation of henzene under liquid-phase conditions to produce ethylbenzene. A further aspect of the invention involves the transalkylation of a feed stock containing a mixture of a polyalkylbenzene component and a benzene component to produce a disproportionation product comprising a monoalkylbenzene. At least a portion of the feed to the transalkylation reaction zone is dehydrated to provide a feed stock, including both the polyalkylbenzene and the benzene components, having a total water content of no more than 100 ppm.

DETAILED DESCRIPTION

Figure 1:
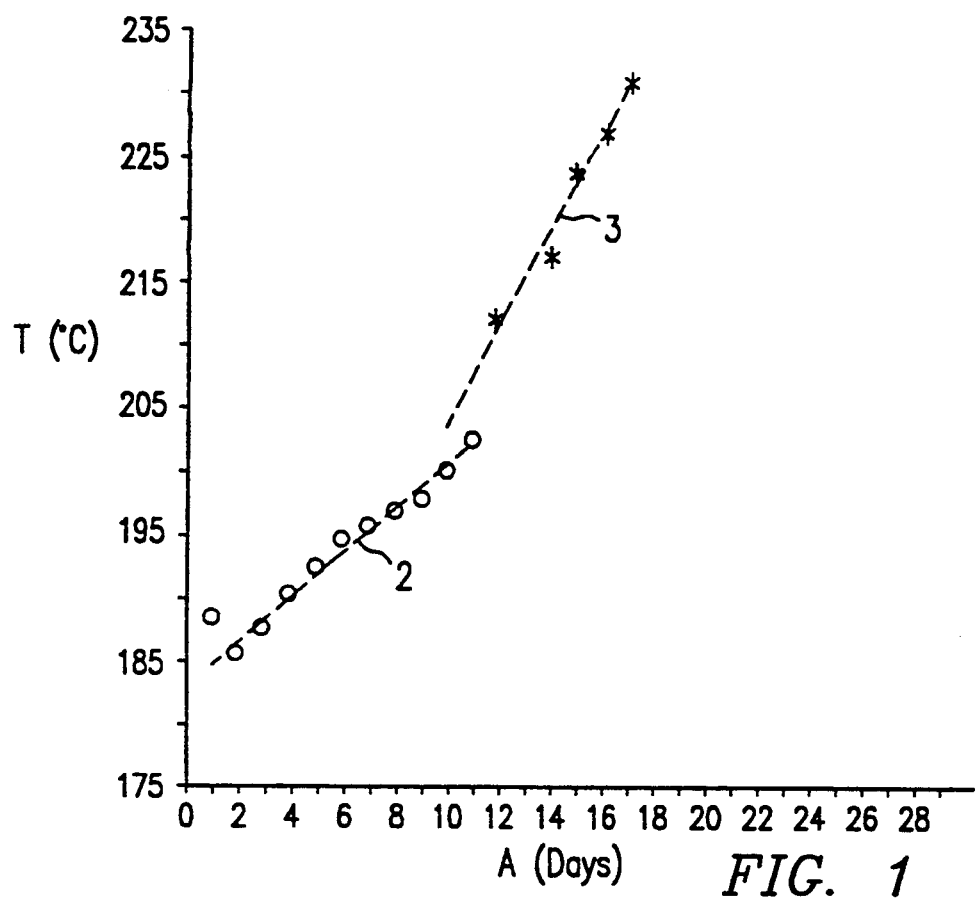
FIG. 1 is a graph showing the results of experimental work involving dehydration of a feed stream to a transalkylation reaction carried out over zeolite omega.

As noted previously, aromatic conversion reactions such as alkylation or transalkylation may be carried out in the vapor phase or in the liquid phase. Intermediate pore sized zeolites such as ZSM-5 (pore size of about 6 angstroms) are effective catalysts for vapor phase alkylation or transalkylation where movement of aromatic molecules in the gas phase through the molecular sieve network takes place by energy vibration. However, somewhat larger pore size molecular sieves appear to be necessary to provide effective catalysts for processes such as the liquid phase alkylation of benzene. Thus, benzene, which has a kinetic diameter of about 5.9 angstroms, will enter into the molecular sieve network of an intermediate pore size molecular sieve such as ZSM-5. However, the resulting alkylated product such as ethylbenzene or cumene will not readily move through the molecular sieve channels by liquid phase displacement.

The zeolite molecular sieves employed in the present invention and having a pore size greater than 6.5 angstroms are effective catalysts under relatively mild conditions for liquid phase hydrocarbon aromatic hydrocarbon conversion reaction such as the ethylation of benzene or the transalkylation of polyethylbenzene. Surprisingly, conversion takes place at relatively low temperature conditions of less than 300° C., about 275° C. or less. In fact, effective ethylation or transalkylation reactions can take place in the liquid phase over the larger pore size zeolite molecular sieves employed in the present invention at temperatures within the range of about 200°–250° C. and such reactions can be accomplished without undesirable side reactions as may be encountered in vapor phase reaction conditions. The pressure on the reaction zone in which the conversion reaction takes place is necessarily above the vapor pressure of the aromatic substrate involved. Preferably, the reaction zone pressure is at least 50 psi above the vapor pressure. Thus, in the ethylation of benzene at 225° C. to produce ethylbenzene, the reactor pressure preferably would be about 350 psig or more. In general, the reactor pressure may range from about 250–1000 psig.

While, as noted previously, water can be tolerated in vapor phase reactions, it does under the high temperature conditions encountered in vapor phase reaction zones effect the dealumination of the catalyst with a corresponding decrease in protonated sites and a reduction in acidic catalyst activity. One would not expect a similar effect to be encountered under the relatively mild conditions of liquid phase aromatic conversion reactions and in fact it appears that dealumination in the presence of water does not occur under these conditions. However, by dehydrating the feed stream to the liquid phase reaction zone, the aging quality of the catalyst is substantially increased. In fact, by decreasing the water content to well below 300 ppm, a value normally tolerated in vapor phase reactions without substantial adverse impact upon catalyst aging quality, the aging quality the catalyst in the liquid phase condition is materially enhanced.

As noted previously, the molecular sieves employed in the present invention have pore sizes greater than 6.5 angstroms which readily accommodate movement of molecules within the molecular sieve network by a liquid phase displacement mechanism. The specific zeolite molecular sieves, zeolites Y, and beta have a pore size within the range of 7.0–7.5 angstroms. The catalysts are not acid extracted to effect dealumination. In experimental work carried out relative to the invention, such larger pore size zeolite molecular sieves were employed as catalysts in the liquid phase transalkylation of diethylbenzene. The catalysts used in the experimental work were zeolites omega and Y. omega is characterized by a one dimensional molecular sieve framework Zeolite Y, is characterized by three dimensional channel system and has an average pore size of about 7.3. Zeolite Y catalysts have silica/alumina ratios of less than 10, usually about 5–6.

In the experimental work carried out employing a first zeolite omega, a mixture of benzene and a polyethylbenzene overheads fraction resulting from a vapor phase alkylation process was passed into a reactor containing zeolite T omega catalyst. The reactor was operated in a flooded, up flow mode configuration and under a pressure of about 30 psig to maintain the aromatic compounds in the liquid phase. The flow rate was sufficient to provide a space velocity (LHSV) based upon the total feed of about 3 hr$^{-1}$. The weight ratio of benzene to polyethylbenzene overheads was about 4. A typical feed composition employed in the experimental work is shown below in Table I.

TABLE I

| | |
|---|---|
| Non-Aromatic | 0.01 |
| Benzene | 78.87 |
| Toluene | 0.00 |
| Ethyl Benzene | 3.40 |
| p-Xylene | 0.01 |
| m-Xylene | 0.02 |
| Styrene | 0.03 |
| o-Xylene | 0.04 |
| Cumene | 1.67 |
| n-Propyl-Benzene | 3.30 |
| m-Ethyl Toluene | 0.15 |
| p-Ethyl Toluene | 0.05 |
| o-Ethyl Toluene | 0.04 |
| 1,3,5-Trimethyl Benzene | 0.07 |
| 1,2,4-Trimethyl Benzene | 0.20 |
| sec-Butyl Benzene | 0.39 |
| 1,2,3-Trimethyl Benzene | 0.32 |
| m-Diethyl Benzene | −7.03 |
| n-Butyl Benzene | 0.29 |
| p,o-Diethyl Benzene | −3.90 |

| TABLE I-continued | |
|---|---|
| Heavies | 0.49 |

The water content of the feed was about 300 ppm. The temperature was progressively increased during the run as necessary to maintain the transalkylation reaction of 70% conversion of diethylbenzeine. Over the first 11 days of the experimental run, the charge of wet feed stock was first passed into a dehydrator filled with a molecular sieve desiccant. The output from the dehydrator was passed to the reaction zone. The dried feed stock was estimated to have a water content of about 30 ppm. Thereafter, and over the remainder of the run, the wet feed was applied directly to the reactor.

The results of the experimental work employing the zeolite omega catalyst are set forth in FIG. 1. In FIG. 1, curves 2 and 3 are graphs of temperature, T in °C. necessary to maintain 70% diethylbenzene conversion plotted on the ordinant versus the age, A, of the catalyst (the duration of the run) in days plotted on the abscissa. As indicated by curve 2 for the dried feed, the catalyst exhibited an aging quality of about 1.8° C. per day (average daily increase in temperature necessary to maintain 70% conversion). Curve 3 of FIG. 1 indicates the aging quality of the catalyst when the feed stream was diverted from the dryer so that the wet feed containing about 300 ppm water was directly applied to the alkylation reactor. As indicated by curve 3, the aging characteristic for the catalyst more than doubled to about 3.9° C./day.

Figure 2:
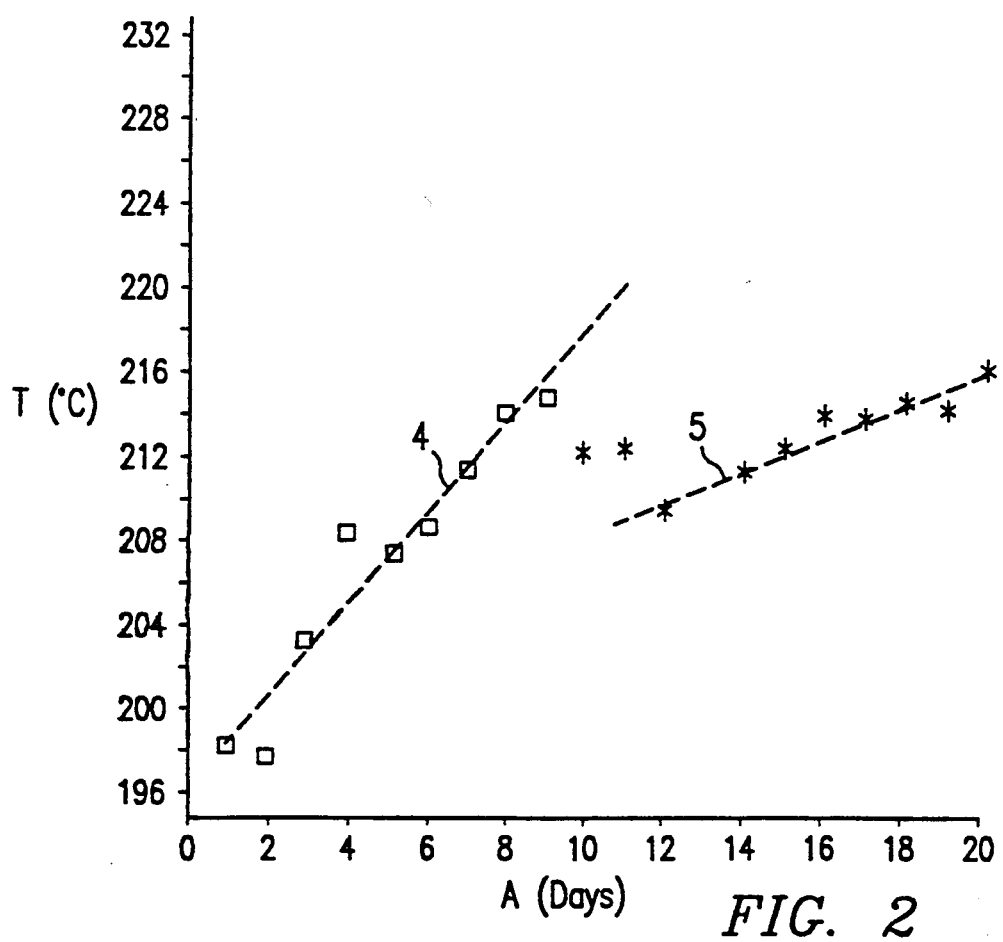
FIG. 2 is a graph showing the results of experimental work involving dehydration of a feed stream to a transalkylation reaction carried out over zeolite Y.

Similar experimental work was carried out using zeolite Y as a catalyst in the liquid phase transalkylation of polyethylbenzene. The feed stock employed here was the same as the feed stock used in the zeolite omega experimental work. In this case the temperature was adjusted as necessary to maintain the transalkylation reaction at 80% conversion of diethylbenzene. The space velocity was the same as employed in the zeolite omega experimental work, 3 hr$^{-1}$ (LHSV). The transalkylation reaction was carried out at a pressure of 300 psig in order to maintain the aromatic hydrocarbons in the liquid phase. In this test, the wet feed, containing about 300 ppm, was initially applied to the reaction vessel containing the zeolite Y. At the conclusion of nine days, the feed stream was first directed to a dehydrator containing silica gel which extracted water from the feed stream to provide a water content of about 30 ppm. The run was then continued for an additional 11 days during which dehydrated feed was supplied to the reaction zone. The results of the experimental work carried out for zeolite Y are illustrated in FIG. 2 in which curves 4 and 5 are graphs of temperature T, in °C., required for 80% diethylbenzene conversion of the wet and dry feeds, respectively, plotted against catalyst age in days. As shown in FIG. 2, the initial wet feed caused a very rapid deactivation of the catalyst. However, at the conclusion of the wet feed injection, the introduction of dry feed not only materially reduced the catalyst deactivation rate but actually enhanced the activity of the catalyst.

In addition to transalkylation, the invention may be employed in the liquid-phase alkylation of aromatic substrates. A particularly important liquid-phase alkylation reaction is the ethylation of benzene under mild liquid phase conditions which results in little or no xylene made. Other liquid phase alkylation reaction may be employed particularly those involving use of $C_2$-$C_4$ alkylating agents. For example, the invention may be employed in the reaction of propylene and benzene to produce cumene. Usually, alkylating agents will take the form of olefins. However, other alkylating agents such as alkines, alkyl halides, alcohols, ethers, and esters as disclosed for example in U.S. Pat. No. 3,551,510 to Pollitzer may be employed. Also aromatic substrates other than benzene for example toluene or xylene, may also be subject to liquid phase alkylation in accordance with the invention.

As noted previously the invention may be carried out employing a zeolite molecular sieve other than zeolite omega and zeolite Y having a pore size within the range of 7.0-7.5 angstroms. Specifically, zeolite beta is an effective alkylation catalyst under the mild temperature conditions involved in liquid phase alkylation. The preferred zeolite beta alkylation catalysts are of a very low sodium content, less than 0.04 weight percent and preferably less than 0.02 weight percent expressed as $Na_2O$. Preferred zeolite beta alkylation catalysts are also characterized in terms of a high surface area of at least 600 $m^2/g$ based upon the crystalline zeolite beta in the catalyst without regard to other components such as binders. The zeolite beta has a silica/alumina ratio of about 20-25.

In the alkylation of benzene, both the benzene feed stock and the ethylene (or other alkylating agent) may contain water. Accordingly, it will be preferred to pass both the benzene and the ethylene through a dehydration unit. While separate dehydrators may be used for the two feed components, usually the ethylene and benzene will be mixed in the mixed feed stream and applied to the dehydration unit and from there to the liquid phase reactor.

In the application of the invention to the transalkylation of polyalkylbenzenes, all or part of the feed to the transalkylation reactor may be subject to a prior dehydration step. Normally the transalkylation of polyalkyl benzenes is carried out in conjunction with in an alkylation step as disclosed, for example, in the aforementioned patent to Barger et al. The output from the alkylation reactor is subjected to one or more separation steps resulting in a polyalkylbenzene component which is combined with benzene and then passed to the transalkylation reaction zone. In the present invention the transalkylation reaction zone is operated under temperature and pressure conditions to effect liquid phase disproportionation of the polyalkylbenzene component to arrive at a disproportionation product having a reduced polyalkylbenzene content and an enhanced monoalkylbenzene component. Typically, the polyalkylbenzene component will contain predominantly dialkylbenzene with a minor amount of trialkylbenzene.

Where the invention involves a transalkylation process carried out in conjunction with a liquid phase alkylation step proceeded by a dehydration step as described above, the polyalkylbenzene component supplied to the transalkylation reactor should be substantially free of water and it normally will be necessary to subject only the benzene component to a dehydration step. However in other applications of the invention, it may be necessary to subject the polyalkylbenzene component to a dehydration step prior to its introduction to the transalkylation reactor. For example, the transalkylation procedure may be carried out in combination with a vapor phase alkylation procedure which tolerates water in the feed stream or in which water is additionally added, for example, as disclosed in the aforementioned patent to Barger et al. In this case it may be necessary to subject both the polyethylbenzene component and the benzene component to dehydration prior to passage to the transalkylation reactor.

Having described specific embodiments of the present invention, it will be understood that modification thereof may be suggested to those skilled in the art, and it is intended to cover all such modifications as fall within the scope of the appended claims.

We claim:

1. In a liquid phase aromatic conversion process, the steps comprising:
   a) supplying a feedstock containing at least one aromatic compound and having water entrained therein to a dehydration zone;
   b) within said dehydration zone removing water from said feedstock to provide a dehydrated feedstock having water content of no more than 100 ppm;
   c) supplying said dehydrated feedstock into a reaction zone containing a zeolite molecular sieve catalyst having a pore size greater than 6.5 angstroms and selected from the group consisting of zeolite Y, and zeolite beta;
   d) operating said reaction zone at temperature and pressure conditions to maintain said aromatic compound in the liquid phase and sufficient to cause said aromatic conversion reaction to proceed in the presence of said catalyst; and
   e) recovering converted product from said reaction zone.

2. The method of claim 1, wherein said dehydrated feed stock has a water content of no more than 50 ppm.

3. The method of claim 1, wherein said catalyst has a pore size within the range of 7.0–7.5 angstroms.

4. The method of claim 1, wherein said catalyst comprises zeolite Y.

5. The method of claim 1, wherein said catalyst comprises zeolite beta.

6. The method of claim 1 wherein said reaction zone is operated at a pressure at least 50 psi above the vapor pressure of said aromatic compound.

7. In a process for the liquid phase alkylation of aromatic compounds, the steps comprising;
   a) supplying a feedstock containing an aromatic substrate and having water entrained therein to a dehydration zone;
   b) within said dehydration zone removing water from said feedstock to provide a dehydrated feedstock having a water content of no more than 100 ppm;
   c) withdrawing said dehydrated aromatic substrate from said dehydration zone and passing said substrate into a reaction zone and containing an alkylation catalyst comprising a zeolite molecular sieve having a pore size greater than 6.5 angstroms;
   d) supplying an alkylating agent to said reaction zone;
   e) operating said reaction zone at temperature and pressure conditions to maintain said aromatic substrate in the liquid phase and under temperature conditions to cause alkylation of said aromatic substrate by said alkylating agent in the presence of said catalyst; and
   f) recovering an alkylated aromatic substrate from said reaction zone.

8. The method of claim 7, wherein said aromatic substrate comprises benzene and said alkylating agent is an ethylating agent or a propylating agent.

9. The method of claim 7, wherein said catalyst has a pore size within the range of 7.0–7.5 angstroms.

10. The method of claim 9, wherein said alkylating agent is an olefin.

11. The method of claim 8, wherein said alkylating agent is ethylene.

12. The method of claim 11, wherein said catalyst has a pore size within the range of 7.0–7.5 angstroms.

13. The method of claim 12 wherein said dehydrated feed stock has a water content of no more than 50 ppm.

14. The method of claim 11, wherein said alkylation catalyst comprises zeolite Y.

15. The method of claim 11 wherein said alkylation catalyst comprises zeolite beta.

16. The method of claim 8 wherein the output from said reaction zone comprises a mixture of monoalkyl and polyalkyl benzenes further comprising subjecting said output from said reaction zone to at least one separation step resulting in a polyalkyl benzene component and supplying said polyalkyl benzene component and benzene to a transalkylation reaction zone containing a transalkylation catalyst comprising the zeolite molecular sieve having a pore size greater than 6.5 angstroms and operating said transalkylation reaction zone under temperature and pressure conditions to effect liquid phase disproportionation of said polyalkyl benzene component in the presences of said transalkylation catalyst to arrive at a disproportionation product having a reduced polyalkyl benzene content and an enhanced monoalkyl benzene component.

* * * * *